United States Patent [19]

Chavkin

[11] Patent Number: 4,613,497
[45] Date of Patent: Sep. 23, 1986

[54] DRY, WATER-FOAMABLE PHARMACEUTICAL COMPOSITIONS

[75] Inventor: Leonard Chavkin, Westfield, N.J.

[73] Assignee: Health Products Development, Inc., Somerville, N.J.

[21] Appl. No.: 584,788

[22] Filed: Feb. 29, 1984

[51] Int. Cl.$^4$ .............................................. A61C 9/04
[52] U.S. Cl. ..................................... 424/44; 514/819; 514/843
[58] Field of Search .......................................... 424/44

[56] References Cited

U.S. PATENT DOCUMENTS 3,947,566  3/1976  Sarna et al. ........................... 424/45
4,187,286  2/1980  Marcus .................................. 424/44
4,309,408  1/1982  Pathak et al. ........................ 424/44
4,322,399  3/1982  Ahmad et al. ........................ 424/44

OTHER PUBLICATIONS

Remington's Pharmaceutical Sciences, 16th ed., 1980.

*Primary Examiner*—Leonard Schenkman
*Attorney, Agent, or Firm*—Omri M. Behr

[57] ABSTRACT

A substantially anhydrous foamable composition capable of forming a substantially stable foam on contact with water is formed from a mixture of water soluble polysaccharide gum, an effervescent base and a biocompatible gelling salt. These compositions upon contact with water form extremely stable foams which are capable of acting as carriers for pharmaceutically active compositions.

15 Claims, No Drawings

DRY, WATER-FOAMABLE PHARMACEUTICAL COMPOSITIONS

BACKGROUND OF THE INVENTION

The use of foams for pharmaceutical purposes is well known particularly in the field of contraception as vaginal foams and in the treatment of hyperacidity as antiacid foams. The effectiveness of both types of foams has been hindered by the short life such foams in the aqueous environment in which both find themselves. While foaming action is quite simple to initiate, the very presence of the environmental aqueous fluids which initiate the foaming serve to rapidly dilute the foam to a point where it no longer exists in this form. A composition capable of foaming rapidly on the one hand but producing a foam with a substantial foam life is a long felt need. Such foaming compositions, provided that they are made of biochemically compatible materials, can be utilized as carriers or sustained release devices for numerous pharmaceutically active compositions.

SUMMARY OF THE INVENTION

It has been found that substantially anhydrous compositions capable of forming a substantially stable foam on contact with water may be formulated from mixtures comprising a water soluble polysaccharide gum, a water soluble biocompatible calcium or potassium gelling salt and an effervescent base comprising an alkali metal carbonate or bicarbonate and a water soluble biocompatible acid or acid salt. Such compositions may be compounded with a predetermined pharmaceutically active material and provided in any of the usual dosage forms such as tablets, capsules, powders, granules, or suppositories. The compositions may then be administered in a conventional manner suitable for their intended purpose. Suitable loci for administration are per os for gastrically active compositions and intravaginally for vaginal contraceptives, buffers and the like.

DESCRIPTION OF THE PREFERRED EMBODIMENTS

The substantially anhydrous foamable compositions of the present invention comprise 20 to 75 parts by weight, suitably about 30 to 50 parts by weight of a water soluble polysaccharide gum. Among the suitable gums may be mentioned the water soluble alginate salts such as sodium or potassium alginate and kappa carrageenan as well as iota carrageenan. There is also provided a gelling agent to provide a rubbery polymer salt, said salt comprising between about 10 to about 50, suitably between about 20 to about 30 parts by weight of the total composition. The gelling salt can be any water soluble biocompatible calcium salt such as the gluconate, lactate, chloride, or less soluble salts if required for slower gelling such as carbonate or phosphate. Where kappa carrageenan is utilized as the polysaccharide gum, the corresponding potassium salts may be employed. It is preferred to utilize an amount of water soluble salt corresponding to between 10 and 100% by weight of the gum in the composition.

The foaming effect is achieved by the presence of an effervescent base (the term base here not being utilized in its meaning sense as opposite or complementary to acid). The base comprises a gas generating component most suitably a carbonate or bicarbonate, preferably sodium or potassium bicarbonate and an acid component selected from any solid water soluble biocompatible acid such as the fruit acids suitably tartaric, malic, fumaric, adipic or citric acids, or acid salts such as sodium biphosphate. In the preferred embodiment of the invention, substantially equal parts by weight of the gas generating component and the acid are utilized.

A large variety of pharmaceutically active compositions can be incorporated into the compositions and the compositions formulated into conventional modes of administration.

For purposes of the following discussion, the standard dosage unit will be considered as comprising one gram of gum, 0.5 grams of alkali metal bicarbonate, 0.5 grams of biocompatible acid, and 0.5 grams of gelling salt. Such a dosage unit is merely considered to be illustrative and no way to be considered as limiting the scope of the present invention.

A vaginal contraceptive composition may be prepared comprising the basic foamable composition and a spermicide. Any known vaginally active spermicide may be employed in particular, there may be mentioned nonoxynol-9, octoxonol or mefengol. These are compounded in dosages of between 50 to 200, suitably between 75 and 100 mg. per dosage unit.

A vaginal buffering agent may be provided by increasing the amount of the biocompatible acid by between 250 and 1,000, most suitably between 300 and 500 mg./dosage unit of acid.

Another use for the compositions may be found as gastric antiacid agents. In this composition, there are additionally utilized carbonates such as calcium or magnesium carbonate or the hydroxides of aluminum, magnesium, or bismuth. These are merely considered to be the common and exemplary materials but other biocompatible bases could also be employed.

The stable nature of the foam produced by the foaming compositions of the present invention makes the foams particularly suitable as gastrio-intestinal depots operating as sustained release agents for a variety of pharmacologically active agents which are traditionally administrable by a gastric route. As exemplifying but not limiting this aspect of the invention may be mentioned sympathomimetic amines such as phenylpropanolamine and salts, ephedrine and salts, isoproterenol and salts, phenylephrine and salts or pseudoephedrine and salts, antihistimes such as chlorpheniramine, diphenhydramine, docylamine, phenyltoloxamine, pyrilamine, tripelenamine, pheniramine, brompheniramine, dexbrompheniramine, dexchlorpheniramine, promethazine, meclizine or cyclizine, antitussives such as dextromethorphan, benzonatate, noscapine, carbetapentane citrate, caramiphen ethane disulfonate, or chlorphedianol, analgesics such as aspirin, acetaminophen, salicylamide, sodium silicylate, indomethacin, ibuprofen or phenylbutazone, and muscle relaxants such as carisoprodol, methocarbamol or meprobamate.

It will be understood by those skilled in the art that pharmaceutically inert excipients, diluents and the like can be included in the compositions as desired.

The special advantage of the compositions of the present invention lies in the desirable combination of immediate action and long life compared to conventional foams. For example, currently available vaginal contraceptives tablets and suppositories require a 10 to 15 minute waiting period for the foam to develop as opposed to the 2 to 5 minute time required by the present compositions, and the present compositions maintain their structure for up to 6 hours as opposed to one hour for conventional products. These two properties are extremely important in considering the esthetics of use as vaginal contraceptives permitting on the one hand substantially instantaneous intercourse where this is desired and on the other hand, an unobvious "pre-planning" if that approach is desired.

SPECIFIC FORMULATIONS

| Material | Mg/dosage Unit |
|---|---|
| EXAMPLE I | |
| Vaginal Contraceptive Composition | |
| Sodium Alginate | 500 |
| Sodium Bicarbonate | 500 |
| Citric Acid | 500 |
| Calcium Gluconate | 200 |
| Nonoxynol 9 | 100 |
| Lactose | 500 |
| TOTAL | 2,300 |
| EXAMPLE II | |
| Vaginal Buffering Agent (pH 4–5) Molded Suppository | |
| Sodium Alginate | 850 |
| Sodium Bicarbonate | 500 |
| Citric Acid | 1,000 |
| Calcium Gluconate | 200 |
| Polyethylene Glycol 1540 | 1,000 |
| Polyethylene Glycol 4000 | 250 |
| TOTAL | 3,300 |

The mixtures of Examples I and II can be granulated to be compressed in a conventional tableting machine.

| EXAMPLE III | |
|---|---|
| Gastric Antiacid Material | |
| Material | Mg/dosage Unit |
| Iota carrageenan | 200 |
| Sodium Bicarbonate | 150 |
| Tartaric Acid | 150 |
| Calcium Carbonate | 100 |
| Aluminum hydroxide | 200 |
| Magnesium hydroxide | 200 |
| TOTAL | 1,000 |

This mixture can be granulated to be compressed in a conventional tableting machine or filled into a powder dispenser.

| EXAMPLE IV | |
|---|---|
| Antihistamine Composition | |
| Formula | Per Dose (2 tablets) |
| Pseudoephedrine Hydrochloride | 120 mg. (a 12 hour dose) |
| Kappa carrageenan | 250 mg. |
| Sodium Bicarbonate | 125 mg. |
| Citric Acid | 125 mg. |
| Potassium Gluconate | 250 mg. |
| TOTAL | 870 mg. or 435 mg. per tablet |

Process

Mix all ingredients, granulate with 75% isopropanol. Dry, lubricate with 1% calcium stearate and compress into tablets.

In accordance with the above procedure but in place of pseudoephedrine hydrochloride, there is utilized chlorpheniramine maleate 12 mg. or dextromethorphan hydrobromide 120 mg., a similar product (2 tablets, 12 hr. dose) is obtained.

| EXAMPLE V | |
|---|---|
| Gastric Antiacid Tablet | |
| Formula | Per Dose (Film Coated Tablet) |
| Potassium Bicarbonate | 500 mg. (5 meq. K) |
| Citric Acid | 150 mg. |
| Sodium Alginate | 250 mg. |
| Dicalcium Phosphate dihydrate | 100 mg. |

Process

Granulate and compress as in Example I. Film coat tablets for easy swallowing.

| EXAMPLE VI | |
|---|---|
| Analgesic Composition | |
| Formula | Per Dose (2 tablets) |
| Acetaminophen, powder | 1,300 mg. (an 8 hr. dose) |

A composition is prepared in accordance with Example IV but substituting acetaminophen for pseudoephidrine.

Two tablets provide sustained blood levels of acetaminophen over an eight hour period equal to two divided doses of 650 mg. each at four hour intervals.

| EXAMPLE VII | |
|---|---|
| Muscle Relaxant Composition | |
| Formula | Per Dose (2 tablets) |
| Carisoprodol, powder | 700 mg. (a 12 hr. dose) |

A composition is prepared in accordance with Example IV but substituting acetaminophen for pseudoephidrine.

Two tablets provide sustained blood levels of carisoprodol over an eight hour period equal to two divided doses of 350 mg. each at four hour intervals.

| EXAMPLE VIII | |
|---|---|
| Contraceptive Gel for delivery by means of Vaginal Applicator | |
| Material | Mg. Per Dosage Unit |
| Nonoxynol-9 | 100.0 |
| Sodium Alginate | 800.0 |
| Sodium Bicarbonate | 500.0 |
| Citric Acid | 500.0 |
| Polyethylene Glycol 1500 | 1000.0 |
| Calcium Gluconate | 200.0 |
| TOTAL | 3100.0 mg. |

I claim:

1. A substantially anhydrous foamable composition capable of forming a substantially stable foam on contact with water comprising:
   (a) 20–75 parts by weight of a water soluble polysaccharide gum,
   (b) 10 to 50 parts by weight of an effervescent base comprising an alkali metal carbonate or bicarbonate and a water soluble biocompatible acid or acid salt and
   (c) 10% to 100% by weight relative to the weight of gum used, of a soluble biocompatible calcium gelling salt, or potassium gelling salt, to the extent that said proportion of potassium salt is not met by the alkali metal carbonate or bicarbonate of (b) where said alkali metal is potassium wherein;

the gum is selected from the group consisting of sodium or potassium alginate, sodium kappa carrageenan or sodium iota carrageenan, the acid component of the effervescent base is fruit acid or a biocompatible acid salt and the gelling salt is selected from the group consisting of calcium gluconate, lactate, citrate, formate, chloride, provided that where the gum is kappa carrageenan then the salt is the corresponding soluble potassium salt.

2. A sustained release gastric depot composition for the administration of a gastrically administrable pharmaceutically active agent comprising a composition of claim 1 and an effective amount of said pharmaceutically active agent.

3. A composition according to claim 2 wherein the amount of pharmaceutically active agent is between 1 and 50% by weight of the weight of the foamable composition.

4. A gastric antiacid composition of claim 2 comprising said foamable composition and a gastric antiacid material.

5. A composition in accordance with claim 4 wherein the antiacid material comprises at least one member selected from the group consisting of a basic salt of calcium, magnesium, aluminum, bismuth or an hydroxide thereof.

6. A composition of claim 5 wherein the antiacid material comprises between 10 and 40 wt. percent of the foamable composition.

7. A composition in accordance with claim 2 wherein the pharmaceutically active agent is selected from the group consisting of a sympathomimetic amine, an antihistamine, an antitussive, an analgesic and a muscle relaxant.

8. A composition of claim 7 wherein the sympathomimetic amines are selected from the group consisting of phenylpropanolamine, ephedrine, and pseudoephedrine, the antihistamine is chlorpheniramine, the antitussive is dextromethorphan, and the analgesic is acetaminophen.

9. A sustained release vaginal depot composition for the administration of a vaginally administrable pharmaceutically active agent comprising a composition of claim 1 and an effective amount of said pharmaceutically active agent.

10. A composition according to claim 9 wherein the amount of pharmaceutically active composition is between 1 and 50% by weight of the weight of the foamable composition.

11. A contraceptive composition of claim 10 introducable into the female vagina in dry form comprising said foamable composition and between 1 and 50% by weight of said composition of a spermicidally active agent.

12. A composition of claim 11 wherein the spermicide is nonoxynol, octoxonol, or mefengol.

13. A composition of claim 12 wherein the spermicidal composition comprises between 2 and 8% by weight of the foamable composition.

14. A vaginal buffering agent in accordance with claim 9 which comprises said foamable composition and an additional amount of said acid or acid salt.

15. A composition in accordance with claim 14 wherein the amount of acid is between 10 and 40% by weight of the foamable composition.

* * * * *